(12) United States Patent
Ignatyev et al.

(10) Patent No.: US 8,378,157 B2
(45) Date of Patent: Feb. 19, 2013

(54) METHOD FOR PRODUCING BIS(FLUORALKYL)PHOSPHINIC ACID CHLORIDES OR FLUORALKYLPHOSPHONIC ACID CHLORIDES

(75) Inventors: Nikolai (Mykola) Ignatyev, Duisburg (DE); Dana Bejan, Wuppertal (DE); Helge Willner, Muelheim/Ruhr (DE); Emil Aust, Mainz (DE)

(73) Assignee: Merck Patent Gesellschaft mit Beschränkter Haftung, Darmstadt (DE)

( * ) Notice: Subject to any disclaimer, the term of this patent is extended or adjusted under 35 U.S.C. 154(b) by 0 days.

(21) Appl. No.: 13/055,229

(22) PCT Filed: Jun. 24, 2009

(86) PCT No.: PCT/EP2009/004535
§ 371 (c)(1),
(2), (4) Date: Jan. 21, 2011

(87) PCT Pub. No.: WO2010/009791
PCT Pub. Date: Jan. 28, 2010

(65) Prior Publication Data
US 2011/0124921 A1     May 26, 2011

(30) Foreign Application Priority Data
Jul. 25, 2008   (EP) .................................... 08013397

(51) Int. Cl.
*C07C 19/08*    (2006.01)
(52) U.S. Cl. .......................................... 570/124; 568/14
(58) Field of Classification Search ........................ None
See application file for complete search history.

(56) References Cited

U.S. PATENT DOCUMENTS
4,739,057 A * 4/1988 Leone-Bay et al. .......... 544/334

FOREIGN PATENT DOCUMENTS
WO     03087110 A1    10/2003
WO     03087111 A1    10/2003

OTHER PUBLICATIONS

Yagupolski et al. "Zh. Obsh. Khim.", (Russ.), pp. 334-339, 1984, vol. 54, No. 2.
Griffiths, James E. "Trifluoromethylphosphonylchloride, CF3P( ))Cl2: preparation, properties, 19F nuclear magnetic resonance and infrared absorption spectra." (Spectrochimica Acta), pp. 303-310, 1986, vol. 24A.
Mahmood, Tariq and Jean'Ne Shreeve, "New Perfluoroalkylphosphonic and Bis(perfluoroalkyl) phosphinic Acids and Their Precursors." (Inorg. Chem.) pp. 3128-3131, 1986, vol. 25.
Michaelis, A. "Ueber die Verbindungen der Elemente der Stickstoffgruppe mit den Radicalen der aromatischen Reihe." (Justus Liebigs Ann. Chem.), pp. 265-365, 1876, No. 181.
Gutman, V. et al. "Ueber Diamide der Phenylphosphorsaeure." (Eingegangen am.) pp. 836-839, Aug. 8, 1960, No. 91.
Lindner, J. et al. "Lieber aronnatische Halogenphosphine und ihre Eignung zur massanalytischen Wasserbestimmung." (Monatshefte Fuer Chemie), pp. 1-19, 1937, vol. 70.
Lindner, Josef and Marcell Strecker. "Untersuchungen ueber Naphtyl-halogenphosphine und-phosphinsaeuren." (Monatshefte Fuer Chemie), pp. 274-281, 1929, vol. 53, No. 54.
World IP Organization. "International Search Report." PCT/EP2009/004535, Applicant: Merck Patent GMBH, Mailed: Oct. 12, 2009.

* cited by examiner

*Primary Examiner* — Sudhakar Katakam
(74) *Attorney, Agent, or Firm* — Millen, White, Zelano & Branigan, P.C.

(57) ABSTRACT

The invention relates to a process for the preparation of bis (fluoroalkyl)phosphinyl chlorides or fluoroalkylphosphonyl dichlorides by reaction of the corresponding bis(fluoroalkyl) phosphinic acid or fluoroalkylphosphonic acid with aryltetrachlorophosphorane as chlorinating agent.

11 Claims, No Drawings

METHOD FOR PRODUCING BIS(FLUORALKYL)PHOSPHINIC ACID CHLORIDES OR FLUORALKYLPHOSPHONIC ACID CHLORIDES

The invention relates to a process for the preparation of bis(fluoroalkyl)phosphinyl chlorides or fluoroalkylphosphonyl dichlorides by reaction of the corresponding bis(fluoroalkyl)phosphinic acid or fluoroalkylphosphonic acid with aryltetrachlorophosphorane as chlorinating agent.

Processes for the synthesis of phosphinyl chlorides and phosphonyl dichlorides by reaction of phosphinic acids or phosphonic acids with the chlorinating agents $PCl_5$ or $SOCl_2$ are known, for example, from L. D. Quin, "A Guide to organophosphorus Chemistry", Wiley-Interscience, N.Y., 2000 or D. E. C. Corbridge, "Phosphorus An Outline of its Chemistry, Biochemistry and Technology (Second Edition)", Elsevier, Amsterdam-Oxford-N.Y., 1980. These methods have preferably been used for the synthesis of non-fluorinated phosphinyl chlorides and non-fluorinated phosphonyl dichlorides.

L. M. Yagupolskii, N. V. Pavlenko, N. V. Ignat'ev, G. I. Matuschecheva, V. Ya. Semenii, Zh. Obsh. Khim. (Russ.), 54 (1984), 2, 334-339, describe a chlorination of a bis(perfluoroalkyl)phosphinic acid using $PCl_5$, but the bis(perfluoroalkyl)phosphinyl chloride and $POCl_3$ obtained have similar boiling points and work-up is therefore complex.

As an alternative, bis(perfluoroalkyl)phosphinyl chlorides can also be synthesised by oxidation of bis(perfluoroalkyl)chlorophosphines using $NO_2$, as known, for example, from J. E. Griffith, Spectrochim. Acta, Part A, 24A (1968), 303 or T. Mahmood, J. M. Shreeve, Inorg. Chem., 25 (1986), 3128-3131.

Bis(fluoroalkyl)phosphinyl chlorides and fluoroalkylphosphonyl dichlorides are interesting precursors for the synthesis of novel materials, for example ionic liquids. It is therefore desirable to have a synthesis of these compounds available which can be implemented economically and on a large industrial scale in order that these precursors can be prepared in large quantities.

The object of the invention is therefore to develop an improved process for the preparation of bis(fluoroalkyl)phosphinyl chlorides or fluoroalkylphosphonyl dichlorides which meets these requirements.

Surprisingly, it has been found that the use of aryltetrachlorophosphorane as chlorinating agent for the reaction with bis(fluoroalkyl)phosphinic acid or fluoroalkylphosphonic acid achieves this object.

The invention therefore relates to a process for the preparation of bis(fluoroalkyl)phosphinyl chlorides or fluoroalkyiphosphonyl dichlorides by reaction of the corresponding bis (fluoroalkyl)phosphinic acid or fluoroalkylphosphonic acid with an aryltetrachlorophosphorane as chlorinating agent.

The starting compounds bis(fluoroalkyl)phosphinic acid and fluoroalkylphosphonic acid are readily accessible starting from the commercially available tris(fluoroalkyl)difluorophosphoranes, as described, for example, in WO 03/087110 and WO 03/087111.

Of the aryltetrachlorophosphoranes, $ArPCl_4$, phenyltetrachlorophosphorane, for example, is a known reagent which can be prepared starting from commercially available dichlorophenylphosphine ($PhPCl_2$) by reaction with chlorine (A. Michaelis, Justus Liebigs Ann. Chem., 181 (1876), 322).

The abbreviation Ar in the formula $ArPCl_4$ stands, for example, for substituted or unsubstituted phenyl, naphthyl or anthryl. Ar particularly preferably stands for unsubstituted or substituted phenyl.

Substituted phenyl denotes phenyl which is substituted by $C_1$- to $C_{12}$-alkyl, partially fluorinated or perfluorinated $C_1$- to $C_6$-alkyl or $C_3$- to $C_7$-cycloalkyl, $NO_2$, F, Cl, Br, unfluorinated, partially fluorinated or perfluorinated $C_1$-$C_6$-alkoxy or $PCl_4$, for example o-, m- or p-methylphenyl, o-, m- or p-ethylphenyl, o-, m- or p-propylphenyl, o-, m- or p-isopropylphenyl, o-, m- or p-isobutylphenyl, m- or p-tert-butylphenyl, m- or p-nitrophenyl, p-methoxyphenyl, p-ethoxyphenyl, m- or p-(trifluoromethyl)phenyl, m- or p-(trifluoromethoxy)phenyl, o-, m- or p-fluorophenyl, o-, m- or p-chlorophenyl, o-, m- or p-bromophenyl, further preferably 2,3-, 2,4-, 2,5-, 2,6-, 3,4- or 3,5-dimethylphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl, 2,4,5-trimethylphenyl or 2,4,6-trimethylphenyl. Ar is very particularly preferably unsubstituted phenyl.

The aryltetrachlorophosphorane is preferably selected from phenyltetrachlorophosphorane, tolyltetrachlorophosphorane and p-chlorophenyltetrachlorophosphorane. In particular, phenyltetrachlorophosphorane is used.

Straight-chain or branched alkyl groups having 1 to 6 C atoms are, for example, methyl, ethyl, isopropyl, propyl, butyl, sec-butyl or tert-butyl, pentyl, 1-, 2- or 3-methylbutyl, 1,1-, 1,2- or 2,2-dimethylpropyl, 1-ethylpropyl or hexyl or, for straight-chain or branched alkyl groups having 1 to 12 C atoms, extended, for example, by octyl or dodecyl.

Unfluorinated $C_1$-$C_6$-alkoxy corresponds to an alkoxy group of the formula $OC_pH_{2p+1}$, where p=1, 2, 3, 4, 5 or 6, for example methoxy, ethoxy, propoxy, butoxy, pentoxy or hexoxy, where the alkyl groups of the alkoxy groups may be straight-chain or branched. In the case of perfluorinated alkoxy groups, all H atoms of the above-mentioned formula are replaced correspondingly by F. In the case of alkoxy groups which are partially substituted by F, only some H are replaced by F.

Unsubstituted saturated or partially or fully unsaturated cycloalkyl groups having 3-7 C atoms are therefore cyclopropyl, cyclobutyl, cyclopentyl, cyclohexyl, cycloheptyl or phenyl, which may be substituted by $C_1$- to $C_6$-alkyl groups or $PCl_4$.

The reaction can be carried out in an organic solvent, for example in chloroform, dichloromethane or 1,6-dibromohexane, but where the reaction can also be carried out without a solvent. The reaction is particularly preferably carried out without a solvent.

The organic solvent is preferably in dried form.

The reaction is generally carried out with equimolar amounts, i.e. 1 mol of bis(perfluoroalkyl)phosphinic acid and 1 mol of aryltetrachlorophosphorane or 1 mol of fluoroalkylphosphonic acid and 2 mol of aryltetrachlorophosphorane. However, it is also possible to use up to a two-fold excess of aryltetrachlorophosphorane. An excess of 10%, as documented in the examples, is preferably used.

The reaction can be carried out at temperatures of −20° to 200° C., preferably at temperatures of 0° to 150° C. The reaction is particularly preferably carried out at a temperature of 0° C. to room temperature for the synthesis of the bis (fluoroalkyl)phosphinyl chloride. The reaction is particularly preferably carried out at temperatures of room temperature to 80° C. for the synthesis of the fluoroalkylphosphonyl dichloride.

It may furthermore be advantageous to carry out the reaction under inert-gas conditions.

A suitable starting material for the process according to the invention for the preparation of bis(fluoroalkyl)phosphinyl chlorides is, in particular, a compound of the formula I $$R^1R^2P(=O)OH \qquad I,$$

where
R$^1$ and R$^2$ each stand, independently of one another, for straight-chain or branched alkyl groups $C_nF_{2n+1-y}H_y$, where
n denotes 1, 2, 3, 4, 5, 6, 7, 8, 9, 10, 11 or 12 and y denotes 0, 1, 2, 3, 4 or 5, but where y denotes 0, 1 or 2 for n=1 or 2.

This results in bis(fluoroalkyl)phosphinyl chlorides of the formula Ia $$R^1R^2P(=O)Cl \qquad Ia,$$

where
R$^1$ and R$^2$ each stand, independently of one another, for straight-chain or branched alkyl groups $C_nF_{2n+1-y}H_y$, where
n denotes 1, 2, 3, 4, 5, 6, 7, 8, 9, 10, 11 or 12 and y denotes 0, 1, 2, 3, 4 or 5, but where y denotes 0, 1 or 2 for n=1 or 2.

The substituents R$^1$ and R$^2$ may be identical or different. The two substituents R$^1$ and R$^2$ are particularly preferably identical.

In a particular embodiment, the substituents R$^1$ and R$^2$ in formula I or Ia are perfluorinated, i.e. R$^1$ and R$^2$ each stand, independently of one another, for a straight-chain or branched fluorinated alkyl group $C_nF_{2n+1}$, where n=1, 2, 3, 4, 5, 6, 7, 8, 9, 10, 11 or 12.

R$^1$ and R$^2$ in formula I or Ia preferably each stand, independently of one another, for trifluoromethyl, pentafluoroethyl, heptafluoropropyl or linear or branched nonafluorobutyl, very particularly preferably for pentafluoroethyl or linear nonafluorobutyl.

Furthermore, suitable starting materials for the process according to the invention for the preparation of bis(fluoroalkyl)phosphinyl chlorides of the formula Ia are also the salts of the acid R$^1$R$^2$P(=O)OH of the formula I, i.e. salts of the formula [R$^1$R$^2$P(=O)O$^-$]Kt$^{m+}$, where Kt$^{m+}$ is an inorganic cation, preferably Na$^+$, K$^+$, Ca$^{2+}$, Mg$^{2+}$, Zn$^{2+}$, or an organic cation, preferably ammonium or phosphonium, and m=1 or 2.

Preferred ammonium cations are [NH$_4$]$^+$ or tetraalkylammonium cations, where the alkyl groups can have 1 to 6 C atoms and may be straight-chain or branched. The alkyl groups are preferably identical.

Preferred phosphonium cations are tetraalkylphosphonium cations, where the alkyl groups can have 1 to 6 C atoms and may be straight-chain or branched, tetraatylphosphonium cations, where "aryl" corresponds to one of the above-mentioned meanings for Ar, or triarylalkylphosphonium cations, where "aryl" corresponds to one of the above-mentioned meanings and "alkyl" denotes an alkyl group having 1 to 6 C atoms, which may be straight-chain or branched. The alkyl groups or aryl groups in the tetraalkylphosphonium cations or tetraarylphosphonium cations are preferably identical. The aryl groups in trisarylalkyiphosphonium cations are preferably identical.

A suitable starting material for the process according to the invention for the preparation of fluoroalkylphosphonyl dichlorides is, in particular, a compound of the formula II $$R^1P(=O)(OH)_2 \qquad II,$$

where
R$^1$ stands for a straight-chain or branched alkyl group $C_nF_{2n+1-y}H_y$, where
n denotes 1, 2, 3, 4, 5, 6, 7, 8, 9, 10, 11 or 12 and y denotes 0, 1, 2, 3, 4 or 5, but where y denotes 0, 1 or 2 for n=1 or 2.

This results in fluoroalkylphosphonyl dichlorides of the formula IIa $$R^1P(=O)(Cl)_2 \qquad IIa,$$

where
R$^1$ stands for a straight-chain or branched alkyl group $C_nF_{2n+1-y}H_y$, where
n denotes 1, 2, 3, 4, 5, 6, 7, 8, 9, 10, 11 or 12 and y denotes 0, 1, 2, 3, 4 or 5, but where y denotes 0, 1 or 2 for n=1 or 2.

In a particular embodiment, the substituent R$^1$ of the formula II or IIa is perfluorinated, i.e. R$^1$ in each case stands, independently of one another, for a straight-chain or branched fluorinated alkyl group $C_nF_{2n+1}$, where n=1, 2, 3, 4, 5, 6, 7, 8, 9, 10, 11 or 12.

R$^1$ in formula II or IIa preferably stands for trifluoromethyl, pentafluoroethyl, heptafluoropropyl or linear or branched nonafluorobutyl, very particularly preferably for pentafluoroethyl or linear nonafluorobutyl.

Furthermore, suitable starting materials for the process according to the invention for the preparation of fluoroalkylphosphonyl dichlorides of the formula IIa are also the salts of the acid R$^1$P(=O)(OH)$_2$ of the formula II, i.e. salts of the formula [R$^1$P(=O)O$_2$]$^{2-}$ m Kt$^+$, where Kt$^+$ is an inorganic cation, preferably Na$^+$, K$^+$, Ca$^{2+}$, Mg$^{2+}$, Zn$^{2+}$, or an organic cation, preferably ammonium or phosphonium, and m=1 or 2, depending on the charge of the cation used.

Preferred ammonium cations are [NH$_4$]$^+$ or tetraalkylammonium cations, where the alkyl groups can have 1 to 6 C atoms and may be straight-chain or branched. The alkyl groups are preferably identical.

Preferred phosphonium cations are tetraalkylphosphonium cations, where the alkyl groups can have 1 to 6 C atoms and may be straight-chain or branched, tetraarylphosphonium cations, where "aryl" corresponds to one of the above-mentioned meanings for Ar, or triarylalkylphosphonium cations, where "aryl" corresponds to one of the above-mentioned meanings and "alkyl" denotes an alkyl group having 1 to 6 C atoms, which may be straight-chain or branched. The alkyl groups or aryl groups in the tetraalkylphosphonium cations or tetraarylphosphonium cations are preferably identical. The aryl groups in trisarylalkyiphosphonium cations are preferably identical.

The process according to the invention enables a synthesis of bis(fluoroalkyl)phosphinyl chlorides or fluoroalkylphosphonyl dichlorides in a yield which is improved compared with the prior art. Furthermore, this process is suitable for a large-scale industrial synthesis, since the purification and separation of by-products, caused by the aryitetrachlorophosphorane, is simplified and only low equipment complexity is necessary in this respect. The by-product C$_6$H$_5$P(O)Cl$_2$ has, for example, a boiling point of 258° C. at atmospheric pressure according to the literature (Gutmann et al., Monatsh. Chem., 91, 1960, pp. 836-839). This boiling point differs significantly from that of the product, meaning that separation of the by-product is simplified.

Even without further comments, it is assumed that a person skilled in the art will be able to utilise the above description in the broadest scope. Thus, the process according to the invention also facilitates, for example, the preparation of perfluoroalkylcarbonyl chlorides from periluoroalkylcarboxylic acids having 2 to 12 C atoms, preferably having 2 to 8 C atoms, or from salts thereof by reaction with aryltetrachlorophosphorane.

The process according to the invention also facilitates, for example, the preparation of perfluorinated dicarboxylic acid dichlorides from dicarboxylic acids having 3 to 10 C atoms, preferably having 4 to 8 C atoms, or from salts thereof by reaction with aryltetrachlorophosphorane.

The preferred embodiments and examples should therefore merely be regarded as descriptive disclosure which is absolutely not limiting in any way.

EXAMPLES

The NMR spectra were measured on solutions in deuterated solvents at 20° C. in a Bruker Avance 300 spectrometer with a 5 mm $^1$H/BB broadband probe with deuterium lock, unless indicated in the examples. The measurement frequencies of the various nuclei are: $^1$H: 300.13 MHz, $^{19}$F: 282.41 MHz and $^{31}$P: 121.49 MHz. The referencing method is indicated separately for each spectrum or each data set.

Example 1 a) Synthesis of Phenyltetrachlorophosphorane, PhPCl$_4$

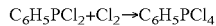
$C_6H_5PCl_2 + Cl_2 \rightarrow C_6H_5PCl_4$ 30.1 g (0.168 mol) of dichlorophenylphosphine in 130 ml of dry chloroform are initially introduced, and 11.9 g (0.168 mol) of chlorine gas are passed in for about 20 minutes, during which the temperature is held at 30° C. The solvent is then removed, giving 40.7 g of a solid, identified as phenyltetrachlorophosphorane.

Melting point: 73-74° C. (lit., 73° C.: J. Lindner, W. Wirth, B. Zaunbauer, Monatsh. Chem., 70 (1937), 1-19).

$^{31}$P NMR (CDCl$_3$; standard: 85% H$_3$PO$_4$), δ, ppm: −42.6 m.

b) Synthesis of Bis(pentafluoroethyl)phosphinyl Chloride

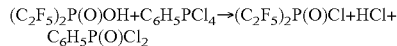
$(C_2F_5)_2P(O)OH + C_6H_5PCl_4 \rightarrow (C_2F_5)_2P(O)Cl + HCl + C_6H_5P(O)Cl_2$ 21.75 g (72 mmol) of bis(pentafluoroethyl)phosphinic acid are added dropwise at room temperature to 20.0 g (80 mmol) of phenyltetrachlorophosphorane, and the mixture is stirred for four hours. Bis(pentafluoroethyl)phosphinyl chloride is separated off by distillation at atmospheric pressure, giving 18.1 g of bis(pentafluoroethyl)phosphinyl chloride, which corresponds to a yield of 78%, based on the phosphinic acid employed.

Boiling point: 86-88° C.

$^{19}$F NMR (pure substance; CD$_3$CN film; standard: CCl$_3$F), δ, ppm: −82:0 s (2CF$_3$), −120.1 d,d (2F$_A$), −124.4 d,d (2F$_B$), $^2J_{P,F(A)}$=92 Hz, $^2J_{P,F(B)}$=100 Hz, $^2J_{F(A),F(B)}$=323 Hz.

$^{31}$P NMR (pure substance; CD$_3$CN film; standard: 85% H$_3$PO$_4$), δ, ppm: 20.8 t,t.

Example 2

Synthesis of Bis(nonafluorobutyl)phosphinyl Chloride

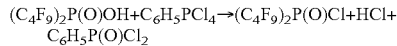
$(C_4F_9)_2P(O)OH + C_6H_5PCl_4 \rightarrow (C_4F_9)_2P(O)Cl + HCl + C_6H_5P(O)Cl_2$ Variant a) 2.49 g (5.0 mmol) of bis(nonafluorobutyl)phosphinic acid are added dropwise at room temperature to a solution of 1.47 g (5.9 mmol) of phenyltetrachlorophosphorane in 3 cm$^3$ of dry chloroform, and the mixture is stirred for a further 50 minutes. Chloroform is separated off by distillation, and bis(nonafluorobutyl)phosphinyl chloride is distilled off at atmospheric pressure, giving 1.62 g of bis(nonafluorobutyl)phosphinyl chloride, which corresponds to a yield of 63%, based on the phosphinic acid employed.

Variant b) The mixture of 4.6 g (18.4 mmol) of phenyltetrachlorophosphorane and 7.3 g (14.5 mmol) of bis(nonafluorobutyl)phosphinic acid is stirred at room temperature for four hours When the evolution of gas (HCl) is complete, the nonafluorobutylphosphonyl dichloride is separated off by distillation at atmospheric pressure, giving 5.73 g of bis(nonafluorobutyl)phosphinyl chloride as colourless liquid substance. This corresponds to a yield of 76%, based on the phosphinic acid employed.

Boiling point: 158-160° C.

$^{19}$F NMR (pure substance; CD$_3$CN film; standard: CCl$_3$F), δ, ppm: −84.3 t,m (2CF$_3$), −115.4 d,d (2F$_A$), −119.7 d,d (2F$_B$), −121.5 m (2CF$_2$), −128.6 m (2CF$_2$), $^2J_{P,F(A)}$=95 Hz $^2J_{P,F(B)}$=102 Hz, $^2J_{F(A),F(B)}$=328 Hz, $^4J_{F,F}$=10 Hz, $^4J_{F,F}$=14 Hz.

$^{31}$P NMR (pure substance; CD$_3$CN film; standard: 85% H$_3$PO$_4$), δ, ppm: 21.8 t,t.

Example 3

Synthesis of Pentafluoroethylphosphonyl Dichloride

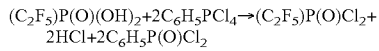
$(C_2F_5)P(O)(OH)_2 + 2C_6H_5PCl_4 \rightarrow (C_2F_5)P(O)Cl_2 + 2HCl + 2C_6H_5P(O)Cl_2$ 6.46 g (32 mmol) of pentafluoroethylphosphonic acid are added dropwise at 0° C. (ice bath) to 19.0 g (76 mmol) of phenyltetrachlorophosphorane with vigorous mixing. The reaction mixture is then stirred at room temperature for four hours. Pentafluoroethylphosphonyl dichloride is separated off by distillation at atmospheric pressure, giving 4.64 g of pentafluoroethylphosphonyl dichloride as colourless liquid substance, which corresponds to a yield of 61%, based on the phosphonic acid employed.

Boiling point: 77-79° C.

$^{19}$F NMR (pure substance; CD$_3$CN film; standard: CCl$_3$F), δ, ppm: −80.9 s (CF$_3$); −122.5 d (CF$_2$), $^2J_{P,F}$=110 Hz.

$^{31}$P NMR (pure substance; CD$_3$CN film; standard: 85% H$_3$PO$_4$), δ, ppm: 17.7 t.

Example 4

Synthesis of Nonafluorobutylphosphonyl Dichloride

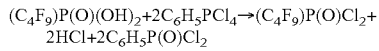
$(C_4F_9)P(O)(OH)_2 + 2C_6H_5PCl_4 \rightarrow (C_4F_9)P(O)Cl_2 + 2HCl + 2C_6H_5P(O)Cl_2$ The mixture of 11.0 g (44 mmol) of phenyltetrachlorophosphorane and 5.5 g (18.3 mmol) of nonafluorobutylphosphonic acid is stirred at 40° C. (bath temperature) for two hours. Nonafluorobutylphosphonyl dichloride is separated off by distillation at atmospheric, pressure, giving 3.77 g of nonafluorobutylphosphonyl dichloride as colourless liquid substance, which corresponds to a yield of 61%, based on the phosphonic acid employed.

Boiling point: 124-126° C.

$^{19}$F NMR (pure substance, CD$_3$CN film; standard: CCl$_3$F), δ, ppm: −83.8 t,m (CF$_3$), −118.5 d (CF$_2$), −121.4 m (CF$_2$), −128.4 m (CF$_2$), $^2J_{P,F}$=113 Hz, $^4J_{F,F}$=10 Hz, $^4J_{F,F}$=14 Hz.

$^{31}$P NMR (pure substance, CD$_3$CN film; standard: 85% H$_3$PO$_4$), δ, ppm: 17.8 t.

The invention claimed is:

1. A process for the preparation of a bis(fluoroalkyl)phosphinyl chloride or a fluoroalkylphosphonyl dichloride which comprises reacting:

the corresponding bis(fluoroalkyl)phosphinic acid of the formula I

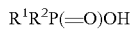
$R^1R^2P(=O)OH$    I, or a salt thereof, where

R$^1$ and R$^2$ each stand, independently of one another, for straight-chain or branched alkyl groups $C_nF_{2n+1-y}H_y$, where n denotes 1-12 and y denotes 0-5, but where y denotes 0, 1 or 2 when n =1 or 2, or the corresponding fluoroalkylphosphonic acid of the formula II $$R^1P(=O)(OH)_2 \qquad \text{II,}$$

or a salt thereof, where $R^1$ is as defined above, with an aryltetrachlorophosphorane as chlorinating agent, wherein the reaction is carried out at a temperature between −20° C. and 200° C.

2. The process of claim 1, wherein the aryltetrachlorophosphorane employed is phenyltetrachlorophosphorane.

3. The process of claim 1, wherein the aryltetrachlorophosphorane is of the formula $ArPCl_4$ wherein Ar stands for substituted or unsubstituted phenyl, naphthyl or anthryl, wherein substituted phenyl denotes phenyl which is substituted by $C_1$- to $C_{12}$-alkyl, partially fluorinated or perfluorinated $C_1$- to $C_6$-alkyl or $C_3$- to $C_7$-cycloalkyl, $NO_2$, F, Cl, Br, unfluorinated, partially fluorinated or perfluorinated $C_1$-$C_6$-alkoxy or $PCl_4$.

4. The process of claim 1, wherein the aryltetrachlorophosphorane is tolyltetrachlorophosphorane or p-chlorophenyltetra-chlorophosphorane.

5. The process of claim 1, wherein the reaction is carried out in an organic solvent selected from chloroform, dichloromethane or 1,6-dibromohexane.

6. The process of claim 1, wherein the reaction is carried out without a solvent.

7. The process of claim 1, wherein the reaction is carried out at a temperature of from 0° C. to 150° C.

8. The process of claim 1, wherein the bis(fluoroalkyl) phosphinyl chloride product is of the formula Ia:

$$R^1R^2P(=O)Cl \qquad \text{Ia,}$$

where $R^1$ and $R^2$ have the meanings stated in claim 1.

9. The process of claim 1, wherein the fluoroalkylphosphonyl dichloride product is of the formula IIa:

$$R^1P(=O)Cl_2 \qquad \text{IIa,}$$

where $R^1$ has the meaning stated in claim 3 claim 1.

10. The process of claim 8, wherein $R^1$ and $R^2$ each stand, independently of one another, for trifluoromethyl, pentafluoroethyl, heptafluoropropyl or linear or branched nonafluorobutyl.

11. The process of claim 9, wherein $R^1$ stands for trifluoromethyl, pentafluoroethyl, heptafluoropropyl or linear or branched nonafluorobutyl.

* * * * *

UNITED STATES PATENT AND TRADEMARK OFFICE
CERTIFICATE OF CORRECTION

PATENT NO. : 8,378,157 B2
APPLICATION NO. : 13/055229
DATED : February 19, 2013
INVENTOR(S) : Nikolai Ignatyev et al.

Page 1 of 1

It is certified that error appears in the above-identified patent and that said Letters Patent is hereby corrected as shown below:

In the Claims

Column 8, line 16, reads "claim 3 claim 1", should read -- claim 1 --.

Signed and Sealed this
Eleventh Day of June, 2013

Teresa Stanek Rea
*Acting Director of the United States Patent and Trademark Office*